United States Patent [19]

Taheri

[11] Patent Number: 5,069,679
[45] Date of Patent: Dec. 3, 1991

[54] METHOD AND APPARATUS FOR REMOVING VENOUS VALVES

[76] Inventor: Syde A. Taheri, 268 Dan Troy, Williamsville, N.Y. 14221

[21] Appl. No.: 435,517
[22] PCT Filed: Feb. 16, 1989
[86] PCT No.: PCT/US89/00634
§ 371 Date: Nov. 13, 1989
§ 102(e) Date: Nov. 13, 1989
[87] PCT Pub. No.: WO89/09029
PCT Pub. Date: Oct. 5, 1989
[51] Int. Cl.⁵ .............................................. A61B 17/32
[52] U.S. Cl. .............................. 606/159; 128/662.06; 128/692; 128/751
[58] Field of Search ............... 606/159, 160–162, 606/170; 604/22, 43, 45, 53; 128/662.05, 662.06, 691, 692, 751

[56] References Cited

U.S. PATENT DOCUMENTS

| 2,655,154 | 10/1953 | Richter | 606/159 |
| 3,704,711 | 12/1972 | Park | 604/284 X |
| 3,837,345 | 9/1974 | Matar | 604/159 |
| 4,200,111 | 4/1980 | Harris | 128/751 |
| 4,601,706 | 7/1986 | Aillón | 604/122 |
| 4,655,217 | 4/1987 | Reed | 606/159 |
| 4,718,425 | 1/1988 | Tanaka et al. | 128/673 |
| 4,739,760 | 4/1988 | Chin et al. | 606/159 |
| 4,765,332 | 8/1988 | Fischell et al. | 606/159 |
| 4,768,508 | 9/1988 | Chin et al. | 606/170 X |
| 4,817,624 | 4/1989 | Newbower | 128/692 |

FOREIGN PATENT DOCUMENTS 0537676 1/1977 U.S.S.R. .............. 606/159

Primary Examiner—John D. Yasko
Assistant Examiner—Adam J. Cermak
Attorney, Agent, or Firm—Sommer, Oliverio & Sommer

[57] ABSTRACT

An improved valvulectome (10) is adapted for use in selectively excising the leaflets of a venous valve. The apparatus includes an elongated probe (11) having one tip end portion (12) adapted to be inserted generally longitudinally into a vein. An actuating rod (55) may be moved relative to the probe to selectively move a pair of blade members (45,46) between their respective fully-retracted positions, at which the blade cutting edges (51,51') will be concealed within the transverse profile or outline of the probe, and their outwardly-extending ready-to-cut positions. The probe has a lumen (38) for sensing the fluid pressure proximate the probe tip. The probe also has a piezoelectric sensor (29) for sensing and measuring the velocity of blood proximate the probe tip. In use, the probe is inserted into a vein, and pushed through a valve with the blades retracted. The blades are then extended radially, and the probe is pulled rearwardly to excise portions of the valve leaflets.

25 Claims, 2 Drawing Sheets

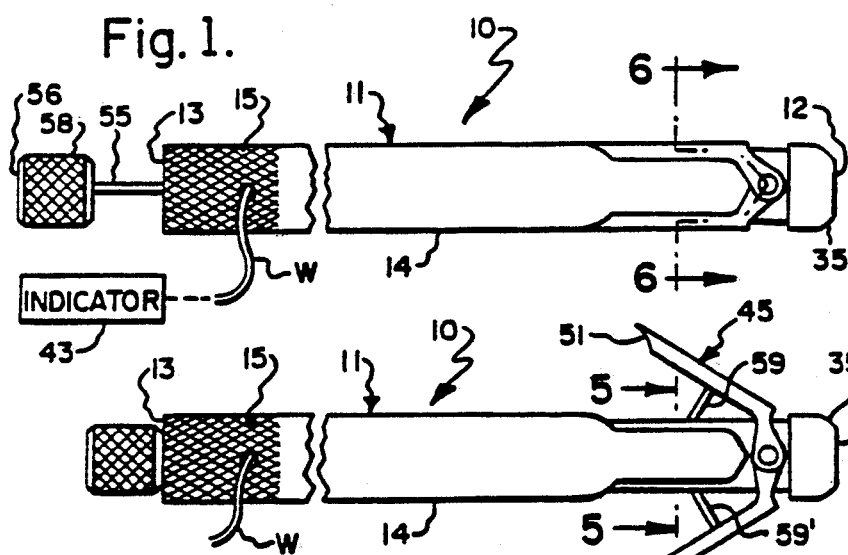
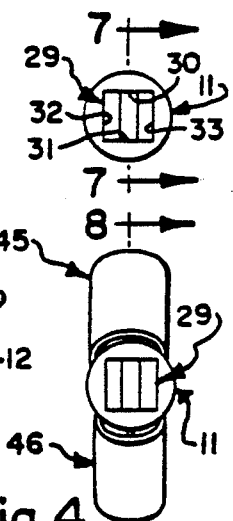
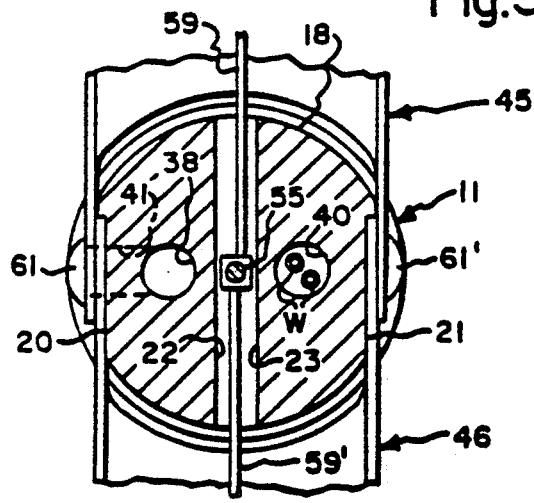
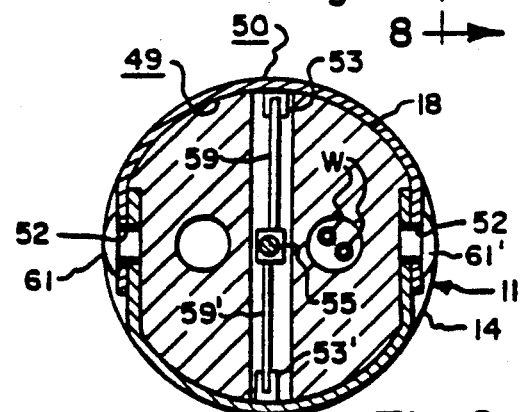
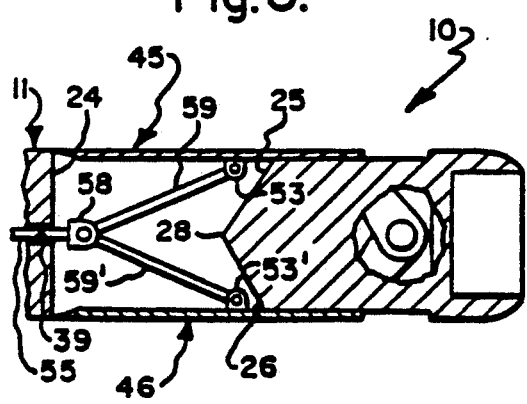
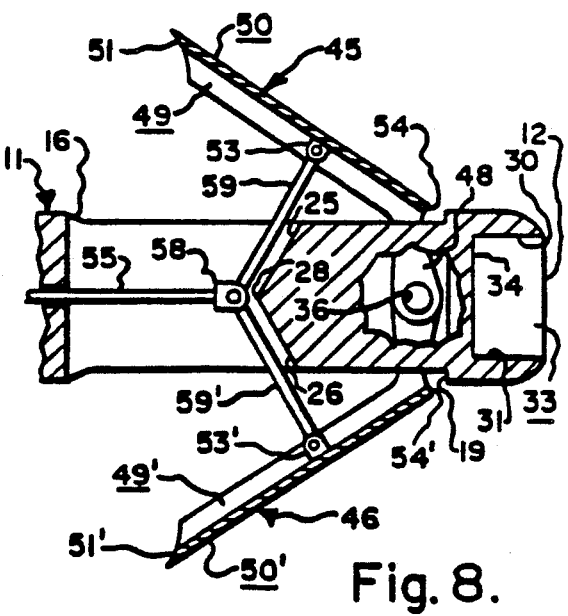

METHOD AND APPARATUS FOR REMOVING VENOUS VALVES

TECHNICAL FIELD

This invention relates generally to apparatus for, and methods of, removing a venous valve from a mammal, and, more particularly, to an improved valvulectome, and method of using same, for selectively excising one or more leaflets of a venous valve.

BACKGROUND ART

It is known that certain veins in the human body contain valves, which largely function as one-way check valves to prevent blood from gathering or pooling in the lower extremities during the normal pumping action of the heart. That pumping action is characterized by alternate contractions and relaxations. During the contractions, blood in the circulatory system is advanced. Thus, as blood is pumped from the lower extremities back toward the heart, these venous valves function to prevent blood from receding due to gravitation during the relaxation phase.

Certain surgical procedures contemplate that a section of a patient's vein be substituted for a section of his artery, which may be deficient for one reason or another (e.g., an aneurysm, blockage, etc.). The use of the patient's own vein avoids problems of tissue-rejection, which often accompanies the use of foreign objects and substances (e.g., various metals or other materials, donor tissue, etc.). Moreover, the presence of foreign substances in the circulatory system may adversely effect the delicate balance of the patient's blood chemistry. However, to substitute a venous section for a corresponding arterial section, it is necessary to excise the venous valve(s) therefrom. At the same time, it would be desirable to minimize the damage to the endothelial tissue lining such vein.

To this end, several surgical techniques have been developed for excising the leaflets of the venous valve in preparation for such arterial substitution. According to one technique, a specially-configured hook-shaped catheter or probe, which somewhat resembles the "poker" of a set of fireplace tools, is provided. This catheter has a greatly-elongated rod-like portion, which is adapted to be inserted generally longitudinally into a vein. A fixed arm projects radially outwardly from the inserted marginal end portion of the probe, adjacent the tip. This arm is provided with a rearwardly-facing radially-extending sharpened cutting edge. Hence, the marginal end portion of the probe is pushed forwardly through the valve to be excised, and is then pulled rearwardly such that the sharpened cutting edge will engage and sever a proximate portion of a valve leaflet. However, upon information and belief, such "push through-and-pull back" manipulation of this probe must be repeated many times with this type of instrument to adequately excise a valve leaflet. Moreover, because of its "poker"-like configuration, the relatively-small inside diameter of the vein, and the fact that the surgeon is often precluded from having an unobstructed view of the inserted marginal end portion of the probe, the use of such probe is believed to unnecessarily damage the endothelial tissue during insertion, reciprocation when actually excising the valve, and subsequent withdrawal.

Other types of known prior art devices are shown in U.S. Pat. Nos. 4,601,706 (Aillón), 4,768,508 (Chin et al.), 4,739,760 (Chin et al.) and 4,722,258 (Marangoni et al.).

SUMMARY OF THE INVENTION

The present invention broadly provides improved apparatus for use in selectively excising one or more leaflets of a venous valve, and also provides an improved method for the use of such probe.

The improved apparatus broadly includes: an elongated probe having one end adapted to be inserted generally longitudinally into a vein, having another end adapted to remain outside the vein, and having an outer surface extending between such ends; recess means forming a recess extending into the probe from the outer surface adjacent the inserted end; at least one blade member movably mounted on the probe, the blade member having a cutting edge; actuating means mounted on the probe and selectively operable to cause the blade member to move relative to the probe between an outwardly-extended position, in which the cutting edge is arranged outwardly beyond the probe outer surface, and inwardly-retracted position, in which the cutting edge is arranged within the recess and is preferably concealed within the outline or profile of the probe outer surface. Thus, when the blade member is in its retracted position, the cutting edge thereof will not extend outwardly beyond the probe outer surface, such that the probe may be moved longitudinally relative to a vein without causing undue damage to the endothelial tissue of the vein. Moreover, such probe may further incorporate means for sensing the fluid pressure proximate the probe tip and/or measuring the velocity of the blood flow.

In use, such apparatus performs an improved method of excising a venous valve by means of a probe having one end adapted to be inserted generally longitudinally into a vein, having another end adapted to remain outside the vein, and having an outer surface, the probe having a recess extending into the probe from its outer surface adjacent its inserted end, having at least one blade member movably mounted on the probe, the blade member having a cutting edge, and having actuating means mounted on the probe and selectively operable to cause the blade member to move relative to the probe between an outwardly-extended position, in which the cutting edge is arranged outwardly beyond the probe outer surface, and an inwardly-retracted position, in which the cutting edge is arranged within the recess and concealed by the profile (when viewed in transverse cross-section) of the probe outer surface. The improved method broadly includes the steps of: making an incision in a vein; moving the blade member to its inwardly-retracted position (if not already in such position) such that the cutting edge will not extend outwardly beyond the probe outer surface; inserting the probe into the vein and through a venous valve to be excised; moving the blade member from such retracted position to its outwardly-extended position; and selectively moving the probe generally longitudinally relative to the vein with the blade member in such outwardly-extended position so as to sever portions of the leaflets of a venous valve within the vein. This method may include the further steps of thereafter subsequently moving the blade member from its outwardly-extended position to its inwardly-retracted position; selectively withdrawing the probe from the vein; and suturing, or otherwise closing, the incision initially formed in the vein. In addition, the improved method may further indicate the step(s) of: measuring the fluid (i.e., blood) pressure and/or velocity proximate the inserted tip end of the probe before, during and/or after the cutting step.

The improved apparatus may also be used to enlarge, reshape or modify the internal wall of an arterial section, for example, for bypass purposes.

Accordingly, the general object of this invention is to provide improved apparatus for selectively excising the leaflet(s) of a venous valve and/or reshaping and arterial section.

Another object is to provide improved apparatus for selectively excising the leaflet(s) of a venous valve and measuring the fluid pressure or velocity proximate the inserted marginal end portion of a probe tip.

Another object is to provide an improved method of excising the venous valve from the vein of a mammal.

Another object is to provide an improved method of excising such a venous valve and measuring the fluid pressure and/or velocity proximate the tip end of a probe inserted into the vein.

Still another object is to provide an improved method and apparatus for selectively removing the venous valve from the vein of a mammal, while minimizing damage to the endothelial tissue lining such vein.

These and other objects and advantages will become apparent from the foregoing and ongoing written specification, the drawings, and the appended claims.

BRIEF DESCRIPTION OF THE DRAWINGS

FIG. 1 is a side elevation of the improved valvulectome, showing the blade members as being in their inwardly-retracted positions.

FIG. 2 is a right end elevation of the valvulectome shown in FIG. 1.

FIG. 3 is a side elevation of the improved valvulectome shown in FIG. 1, but showing the blade members as having been moved to their outwardly-extended ready-to-cut positions.

FIG. 4 is a right end elevation of the valvulectome shown in FIG. 3.

FIG. 5 is a fragmentary transverse vertical sectional view thereof, taken generally on line 5—5 of FIG. 3, showing the probe in transverse cross-section with the blade members in their outwardly-extended positions.

FIG. 6 is a fragmentary transverse vertical sectional view thereof, taken generally on line 6—6 of FIG. 1, again showing the probe in transverse cross-section, but showing the blade members as being in their inwardly-retracted positions.

FIG. 7 is a fragmentary longitudinal vertical sectional view thereof, taken generally on line 7—7 of FIG. 1.

FIG. 8 is a fragmentary longitudinal vertical sectional view thereof, taken generally on line 8—8 of FIG. 4.

MODE(S) OF CARRYING OUT THE INVENTION

Figure 9:
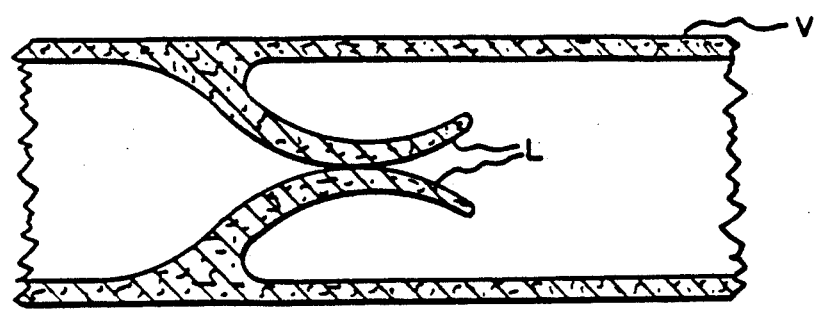
FIG. 9 is a schematic fragmentary longitudinal vertical sectional view of a portion of vein, showing a venous valve therein.

At the outset, it should be clearly understood that like reference numerals are intended to identify the same structural elements, portions or surfaces consistently throughout the several drawing figures, as such elements, portions or surfaces may be further described or explained by the entire written specification, of which this description is an integral part. The drawings are intended to be read (e.g., cross-hatching, arrangement of parts, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Unless otherwise indicated, the terms "inwardly" and "outwardly" refer to the orientation of a surface relative to its axis of elongation, or axis of rotation, as appropriate.

Referring now to the drawings, and, more particularly, to FIGS. 1-4 thereof, this invention broadly provides improved apparatus for, and methods of, excising a venous valve, for example, prior to re-use of a section of such vein, or for other purposes. The improved apparatus is appropriately denominated a "valvulectome" (i.e., apparatus for excising a venous valve). The two aspects of this invention (i.e., the apparatus per se, and the method of its use) will be described seriatim herebelow.

STRUCTURE

As best shown in FIGS. 1-8, the preferred form of the improved apparatus, generally indicated at 10, broadly includes a horizontally-elongated rod-like probe 11 having a planar vertical right end face 12 adapted to be inserted into a patient's vein and be moved generally longitudinally therealong to the situs of a venous valve, having an annular vertical left end face 13 adapted to remain outside the vein, and having an outwardly-facing cylindrical surface 14 extending therebetween. The marginal portion of the outer surface adjacent left end face 13 may be suitably knurled or otherwise roughened, as indicated at 15, to improve the surgeon's grip thereon and his ability to manipulate the probe within and relative to the patient's vein.

Referring now to FIGS. 5-8, an annular recess is depicted as extending into the probe from its outer surface 14 adjacent to, but spaced longitudinally from, right end face 12. As best shown in FIG. 8, this recess is sequentially bounded by a rightwardly-facing annular vertical surface 16 extending radially into the probe from outer surface 14, an outwardly-facing horizontal cylindrical surface 18 extending rightwardly therefrom, and a leftwardly-facing annular vertical surface 19 extending radially outwardly therefrom to rejoin probe outer surface 14. Recess bottom surface 18 is shown as being further provided with a pair of parallel horizontally-spaced longitudinally-extending vertical chordal "flats" 20, 21, which severally occupy opposed arcs of about 60° (FIGS. 5 and 6), and provide deepened opposed portions of the recess to accommodate and conceal the head portions of pivot pin, by which the blade members are pivotally mounted on the probe.

Still referring principally to FIGS. 5–8, a vertically-elongated slot extends diametrically through the probe recess and opens onto recess surface 18 at diametrically-spaced locations. The vertical axis of this slot is substantially parallel to the recess "flat" surfaces 20, 21. Thus, when viewed in transverse cross-section (FIGS. 5 and 6), this slot is seen as being defined between horizontally-spaced planar vertical side surfaces 22, 23, the upper and lower marginal ends of which join recess bottom surface 18. However, when viewed in longitudinal cross section (FIGS. 7 and 8), this recess is seen as being bounded by a rightwardly-facing vertical left end wall 24, and leftwardly-facing pointed right end wall. This right end wall sequentially includes an upwardly- and leftwardly-facing inclined planar surface 25 extending downwardly from an upper portion of recess bottom surface 18, and a downwardly- and leftwardly-facing inclined planar surface 26 continuing downwardly from surface 25 to rejoin recess bottom surface 18 at a lower portion thereof. Thus, surfaces 25, 26 would normally intersect to form a leftwardly-facing transversely-extending horizontal line, indicated at 28. However, in the preferred embodiment, line 28 is shown as being somewhat rounded.

Referring now to FIGS. 2, 3, 7 and 8, a second recess extends axially into the probe from its right end face, to receive and accommodate a piezoelectric sensor, generally indicated at 29 in FIGS. 2 and 4, by which the velocity of blood flowing in the vein may be sensed and measured. More particularly, this second recess has a rectangular transverse cross-section, and is bounded by facing opposed upper and lower planar horizontal surfaces 30, 31, and opposed facing lateral planar vertical surfaces 32, 33. Each of these recess surfaces extends leftwardly into the probe tip from its right end face 12, and terminates in a rightwardly-facing planar vertical common bottom surface 34. An annular rounded surface 35 tangentially joins right end face 12 and probe outer surface 14. A horizontal hole 36, generally perpendicular to "flats" 20, 21, extends diametrically through the probe tip behind, or leftwardly of, the second recess, and opens onto recess surface 18.

As best shown in FIGS. 5–8, the probe is provided with the three horizontally-spaced longitudinally-extending lumens or passageways, severally indicated at 38, 39 and 40. Left lumen 38 communicates with a location on probe outer surface 14 between surfaces 19 and 35 via radial branch passage, indicated by the dashed line 41 in FIGS. 5 and 6. The other end of this first lumen opens onto an appropriate surface of that portion of the probe which remains outside the vein (i.e., end face 13, or a marginal portion of outer surface 14 adjacent end face 13). The purpose of this first lumen is to provide an internal passageway in the probe which allows the fluid pressure at or proximate the probe tip (i.e., at the location where branch passage 41 opens on to recess surface 14) to be monitored and measured by a suitable instrument (not shown) located outside the vein.

The middle lumen 39 axially communicates left end face 13 with slot surface 24.

Right lumen 40 communicates recess bottom surface 34 with probe outer surface 14. This third lumen thus provides a passageway for the passage of electrical wires W communicating sensor 29 with a suitable indicating instrument 43. This instrument may, for example, be a "Directional Doppler", Model 806-A, manufactured by Parks Medical Electronics, Inc., Beaverton, Oreg. 97075.

In the preferred embodiment, upper and lower blade members 44, 45, respectively, are mounted on the probe for selective simultaneous pivotal movement relative thereto between inwardly-retracted or concealed positions, as shown in FIGS. 1, 2, 6 and 7, and outwardly-extended ready-to-cut positions, as shown in FIGS. 3, 4, 5 and 8. The upper blade member is shown as being somewhat saddle-shaped, and has a thin-walled cylindrically-segmented body portion 46. Two horizontally-spaced stirrup-like leg portions, severally indicated at 48, depend vertically from the right margin of body portion 46. The body portion occupies an arc of about 130°, when viewed in transverse cross-section (FIGS. 5 and 6), and has a concave cylindrically-segmented inner surface 49 arranged to be moved pivotally toward and away from probe recess surface 18, and an opposite concave cylindrically-segmented outer surface 50. The radius of blade member inner surface 49 is substantially equal to the radius of recess surface 18 such that, when the blade is in its retracted position, these two surfaces will substantially engage one another in area contact. The radial thickness of the body portion (i.e., between surfaces 49, 50) is substantially equal to the radial depth of the probe recess (i.e., between surfaces 14, 18). Blade member outer surface 50 has substantially the same radius as probe outer surface 14. The leftward end of the blade member which faces away from insertable tip end 12, is sharpened to provide a rearwardly-facing arcuate cutting edge 51. The leg portions 48 are formed integrally with the body portion, and extend downwardly therefrom so as to be arranged generally parallel to probe recess "flat" surfaces 20, 21. These two leg portions are provided with aligned horizontal through-holes, severally indicated at 52, which are adapted to register with probe hole 36. When the upper blade member is in its retracted position, as shown in FIG. 6, the blade member outer surface is substantially continuous with probe outer surface 14. In other words, in such retracted position, the upper blade member is received within the body recess, and does not substantially extend outwardly beyond probe outer surface 14. Hence, when the blade member is moved to such concealed position within the transverse outline or profile of the probe, its cutting edge will be protectively guarded by the edge formed by probe surfaces 14, 16. Moreover, a clevis member 53 is shown as being mounted on concave surface 49 at a location between rearwardly-facing cutting edge 51 and forwardly-facing end face 54. As shown in FIG. 6, clevis member 53 is adapted to be received in the diametrical slot provided through the probe, when the upper blade member is moved to its retracted position.

The lower blade member 46 is substantially identical to the upper blade member, except that its leg portions are positioned between the upper blade member leg portions and probe "flats" 20, 23. Whereas the body portion of the upper blade member occupies an arc of about 130°, the body portion of the lower blade member occupies an arc of about 115°. Moreover, the lower blade member is mounted on the probe at a location diametrically opposite the location of the upper blade, and therefore appears substantially as a mirror image of the same. Because the upper and lower blade members are substantially identical, save for the differences enumerated above, the primes of the same reference numerals used to describe the upper blade member, have been used to identify the corresponding parts, portions or surfaces of the lower blade member.

In the preferred embodiment, the actuating means is a greatly-elongated rod-like member 55 slidably arranged in middle lumen 39. The left end of rod 55 extends leftwardly beyond probe left end face 13. A knob 56, also preferably having a knurled outer surface 57, is suitably secured to the left marginal end portion of the actuating rod, and provides a means by which the surgeon may selectively move the actuating rod relative to the probe. The right end of rod 55 extends past surface 16 into the probe slot. As best shown in FIGS. 7 and 8, a clevis-like member 58 is suitably mounted or otherwise secure to the right marginal end portion of the actuating rod. A pair of connecting links 59, 59' have their marginal end portions pivotally connected to rod clevis member 58, and have their right marginal end portions pivotally connected to blade clevis members 53, 53', respectively. Thus, when the actuating rod is moved leftwardly relative to the probe, rod clevis member 58 will be moved toward probe slot surface 24, and the blade members will be moved toward their fully-retracted positions, as shown in FIG. 7. Conversely, when the actuating rod is moved rightwardly relative to the probe, the rod clevis member 58 will be moved away from slot surface 24, and the blade members will be moved toward their outwardly-extended positions, as shown in FIG. 8. The abutment of rod clevis member 58 against slot nose 28 provides a limit to such outward pivotal movement of the blade members.

As best shown in FIG. 6, a pin 60 is operatively arranged in probe hole 36 and through blade member holes 52, with its opposite head portions, severally indicated at 61, 61', operatively concealed within the recess. Hence, when the blade members are in their fully-retracted positions, the probe emulates a horizontally-elongated cylindrical rod, with substantially no portion extending outwardly beyond the cylindrical outer surface thereof.

OPERATION

The operation of the improved valvulectome is comparatively illustrated in FIGS. 9–13.

FIG. 9 is a schematic longitudinal vertical sectional view of a vein V, showing the leaflets L therein.

Figure 10:
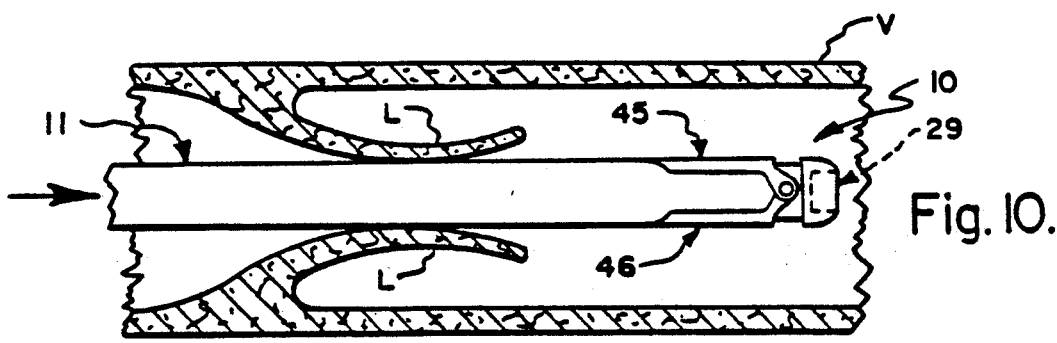
FIG. 10 is a schematic view generally similar to FIG. 9, but showing the inserted marginal end portion of the probe, with the blade members being in their retracted positions, as having been pushed rightwardly through the venous valve so as to spread or dilate the valve leaflets.
Figure 11:
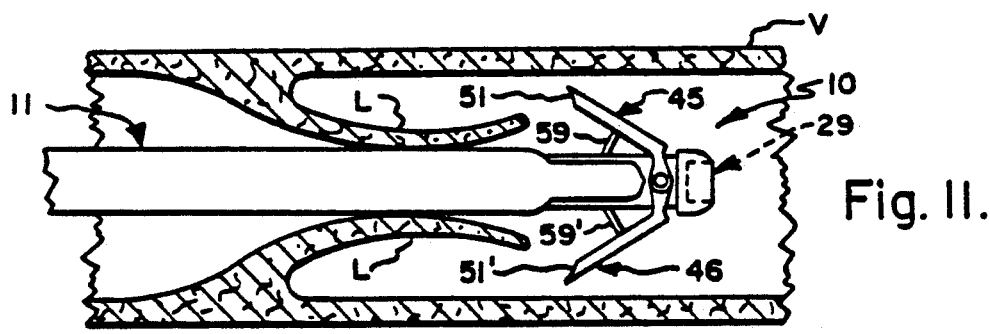
FIG. 11 is a schematic view generally similar to FIG. 10, but shows the blade members as having been moved to their outwardly-extended ready-to-cut positions, and also shows the probe as having been pulled leftwardly from the position shown in FIG. 10.
Figure 12:
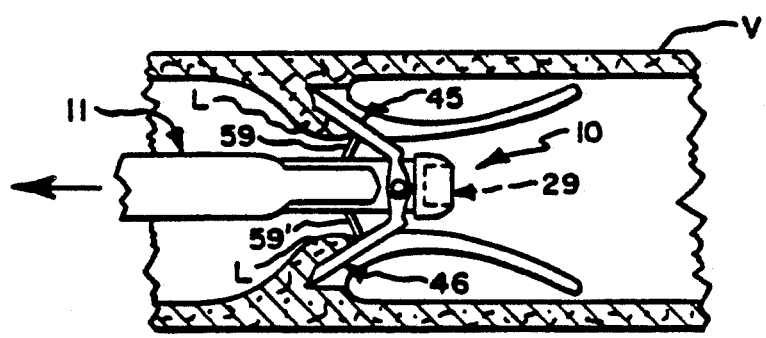
FIG. 12 is a view generally similar to FIG. 11, but shows the probe as having been pulled further leftwardly from the position shown in FIG. 11, and as cutting or excising the leaflets of the venous valve.

To use the improved device, the surgeon first makes a suitable incision (not shown) in the vein, downstream of the valve-to-be-excised. The surgeon may then grasp knob 56, and pull it rearwardly relative to the probe to insure that the blade members will be in their fully-retracted positions (if not already in such positions), as shown in FIG. 7. Thereafter, the surgeon may insert the right or forward marginal end portion of the probe into the patient's vein through the incision, and move it generally longitudinally therealong such that the marginal tip portion will actually pass through the valve, by spreading or dilating the leaflets thereof, as shown in FIG. 10. The surgeon may then simply push the actuating knob rightwardly relative to the probe, to cause the two blade members to move from their inwardly-retracted positions to their outwardly-extended positions, as shown in FIG. 11. Thereafter, the surgeon may pull the probe (with the blade members in such outwardly-extended positions) rearwardly, so as to cause the cutting edges of the blade members to engage and sever proximate portions of the valve leaflets, as shown in FIG. 12. If one pass is not enough, the surgeon may then simply retract the blade members, push the probe tip back through the valve, rotate the probe to another angular position relative to the vein, extend the blade members, and again pull the probe rearwardly to excise another portion(s) of the leaflet(s).

At the same time, the surgeon may suitably position the probe tip, either before, during or after the excision or cutting step, and may determine via left lumen 38, the pressure of blood proximate the probe tip. This feature is deemed particularly useful in order that the surgeon might determine or corroborate that all side conduits or branch venous passages have been either tied or otherwise occluded. In connection with this, the surgeon may also monitor the velocity of the blood flow at the probe tip by means of sensor 29. Thus, the velocity of the blood flow, together with the pressure readings, may be used to corroborate that all side passages have been effectively closed or otherwise occluded.

Figure 13:
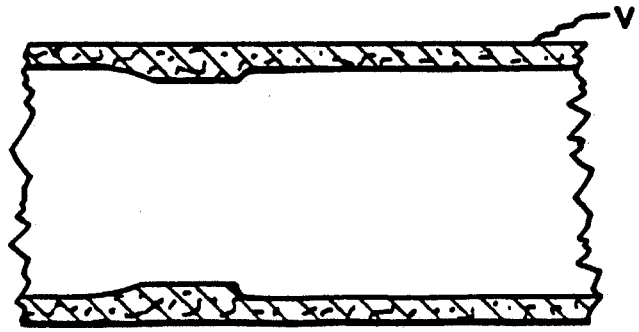
FIG. 13 is a view generally similar to FIG. 12, and shows the condition of the vein after the probe and severed leaflets have been removed.

Once the leaflets have been excised, the surgeon may then pull knob 56 to again move the blade members back to their fully-retracted positions. Once in their concealed positions, the surgeon may then axially withdraw the probe tip from the patient's vein, and either suture or otherwise close the incision, or sever and remove the affected venous section for another surgical procedure. FIG. 13 is a schematic view showing the internal configuration of the vein after the leaflets have been excised.

MODIFICATIONS

The present invention contemplates that many changes and modifications may be made to the structure of the improved valvulectome. For example, the valvulectome may be provided with one or more cutting blades. In the preferred embodiment, two of such cutting blades are provided, but a greater number could alternatively be provided. In the preferred embodiment, the blade members are pivotally mounted on the probe, but this is not invariable. Indeed, while a simple mechanical device (i.e., actuating rod 55) is employed to selectively move the blade members between their fully-extended and fully-retracted positions, other means and mechanisms may be substituted therefor. For example, the actuating means could be mechanical, electrical, pneumatic, hydraulic, or a combination of these.

Moreover, in the preferred embodiment, the piezoelectric velocity sensor is located in the inserted end of the probe. However, the position of such sensor, be it a piezoelectric devise or otherwise, is not limited to this particular position on the probe. If desired, such sensor could be arranged to have its sensing face arranged generally in a radial direction or be it inclined at some positive or negative angle with respect to the flow of blood.

Moreover, the improved probe uses the middle lumen for accommodating the actuating rod, the left lumen for accommodating pressure measurement, and the right lumen for accommodating passage of electrical wires or conductors by which the piezoelectric sensor communicates with the indicator. If the pressure-sensing and/or velocity-sensing features are eliminated, the corresponding lumen may also be eliminated.

Moreover, in the preferred embodiment, the general intent is to conceal the cutting edges within the transverse cross-sectional profile or outline of the probe, when the blade members are in their fully-retracted positions. That transverse outline or profile is shown as being a cylindrical surface in the preferred embodiment. However, in other forms, the probe outer surface may have other configurations. Similarly, while it is presently preferred to pivotally mount the blade members on the probe, in other embodiments, it may be possible to provide for alternative mountings.

The improved apparatus may also be used to cut, redefine or reshape the interior wall of an arterial section (i.e., a length of an artery), if desired. If used for this purpose, the shape of the cutter blades can be modified so as to selectively excise a portion of such arterial wall, such as prior to a bypass or in conjunction with other coronary or femoral surgery.

Therefore, while the presently-preferred embodiment of the improved method and apparatus have been shown and described, and certain modifications thereof discussed, persons skilled in this art will readily appreciate that various additional changes and modifications may be made without departing from the spirit of the invention, as defined and differentiated by the following claims.

I claim:

1. A valvulectome adapted for use in excising a venous valve, comprising:
   an elongated probe having one end adapted to be inserted generally longitudinally into a vein, having another end adapted to remain outside said vein, and having an outer surface extending between said ends;
   recess means forming a recess extending into said probe from said outer surface adjacent said one end;
   a blade member having one end pivotally connected to said probe, said blade member having a cutting edge arranged at another end thereof to face toward said probe other end;
   actuating means mounted on said probe and selectively operable to cause said blade member to move relative to said probe between an outwardly-extended position in which said cutting edge is arranged outwardly beyond said outer surface, and an inwardly-retracted position in which said cutting edge is arranged within said recess;
   whereby, when said blade member is in such retracted position, said cutting edge thereof will not extend outwardly beyond said outer surface, such that said probe may be moved longitudinally relative to said vein without causing undue damage to the endothelial tissue of said vein.

2. A valvulectome as set forth in claim 1 wherein said probe outer surface has a substantially-cylindrical portion.

3. A valvulectome as set forth in claim 1 wherein said cutting edge is arcuate.

4. A valvulectome as set forth in claim 3 wherein said cutting edge is configured as a circular segment.

5. A valvulectome as set forth in claim 1 wherein said probe is provided with a first lumen communicating said recess and said other end, and wherein said actuating means includes an actuating rod arranged in said first lumen and adapted to be moved longitudinally relative thereto, and includes link means having one end pivotally connected to said actuating rod and having another end pivotally connected to said blade member such that when said actuating rod is moved relative to said probe, said blade member is moved between said outwardly-extended and inwardly-retracted positions.

6. A valvulectome as set forth in claim 5 wherein said probe has a second lumen, and further comprising:
   an opening communicating said second lumen with said outer surface adjacent said probe one end, and
   transducer means for measuring the fluid pressure in said second lumen.

7. A valvulectome as set forth in claim 1 wherein said valvulectome includes two of said blade members, and wherein said actuating means is arranged to selectively cause each of said blade members to move simultaneously between such outwardly-extended and inwardly-retracted positions.

8. A valvulectome as set forth in claim 1, and further comprising:
   a velocity sensor mounted on said probe for measuring the velocity of blood in said vein at the position of said sensor.

9. A valvulectome as set forth in claim 8 wherein said probe has a third lumen, and wherein said velocity sensor includes an indicator arranged outside said vein, said sensor and indicator being connected by at least one electrical conductor, and wherein said electrical conductor is arranged in said third lumen.

10. A valvulectome as set forth in claim 8 wherein said sensor is a piezoelectric element.

11. The method of excising a venous valve by means of a probe having one end adapted to be inserted generally longitudinally into a vein, having another end adapted to remain outside said vein, and having an outer surface, said probe having a recess extending into said probe from said outer surface adjacent said one end, having a blade member movably mounted on said probe, said blade member having a cutting edge, and having actuating means mounted on said probe and selectively operable to cause said blade member to move relative to said probe between an outwardly-extended position in which said cutting edge is arranged outwardly beyond said outer surface, and an inwardly-retracted position in which said cutting edge is arranged within said recess, which method comprises the steps of:
   making an incision in a vein;
   moving said blade member to said inwardly-retracted position such that said cutting edge does not extend outwardly beyond the outer surface of said probe;
   inserting said probe into said vein;
   passing said probe one end portion through said venous valve;
   moving said blade member from such retracted position to said outwardly-extended position; and
   moving said probe generally longitudinally relative to said vein with said blade member in said outwardly-extended position so as to sever portions of the leaflets of said venous valve from said vein.

12. The method as set forth in claim 11, and further comprising the additional step of:
   moving said blade member from said extended position to said retracted position; and
   withdrawing said probe from said vein.

13. The method as set forth in claim 12, and further comprising the additional step of:
   selectively closing the incision formed in said vein.

14. The method as set forth in claim 11, and further comprising the additional step of:

measuring the pressure upstream of said venous valve.

15. The method as set forth in claim 14, and further comprising the additional step of:
   measuring the fluid pressure downstream of said venous valve.

16. The method as set forth in claim 15, and further comprising the additional step of:
   comparing the pressures measured upstream and downstream of said venous valve.

17. The method as set forth in claim 11, and further comprising the additional step of:
   measuring the velocity of the blood flow upstream of the situs of said valve.

18. The method as set forth in claim 17, and further comprising the additional step of:
   measuring the velocity of the blood flow downstream of the situs of said venous valve.

19. The method as set forth in claim 18, and further comprising the additional step of:
   comparing the pressures measured upstream and downstream of said venous valve.

20. Apparatus adapted for use in modifying the internal shape of a blood vessel, comprising:
   an elongated probe having one end adapted to be inserted generally longitudinally into said blood vessel, having another end adapted to remain outside said blood vessel, and having an outer surface extending between said ends;
   recess means forming a recess extending into said probe from said outer surface adjacent said one end;
   a blade member having one end pivotally connected to said probe, said blade member having a sharpened edge arranged at another end thereof to face toward said probe other end;
   actuating means mounted on said probe and selectively operable to cause said blade member to move relative to said probe between an outwardly-extended position in which said sharpened edge is arranged outwardly beyond said outer surface, and an inwardly-retracted position in which said sharpened edge is arranged within said recess;
   whereby, when said blade member is in such retracted position, said cutting edge thereof will not extend outwardly beyond said outer surface, such that said probe may be moved longitudinally relative to said blood vessel.

21. The method of modifying the internal shape of a blood vessel by means of a probe having one end adapted to be inserted generally longitudinally into said blood vessel, having another end adapted to remain outside said blood vessel, and having an outer surface, said probe having a recess extending into said probe from said outer surface adjacent said one end, having a blade member movably mounted on said probe, said blade member having a sharpened edge, and having actuating means mounted on said probe and selectively operable to cause said blade member to move relative to said probe between an outwardly-extended position in which said sharpened edge is arranged outwardly beyond said outer surface, and an inwardly-retracted position in which said sharpened edge is arranged within said recess, which method comprises the steps of:
   making an incision in a blood vessel;
   moving said blade member to said inwardly-retracted position such that said sharpened edge does not extend outwardly beyond the outer surface of said probe;
   inserting said probe into said blood vessel;
   passing said probe one end portion past tissue to be excised from said blood vessel;
   moving said blade member from such retracted position to said outwardly-extended position; and
   moving said probe generally longitudinally relative to said blood vessel with said blade member in said outwardly-extended position so as to excise said tissue from said blood vessel.

22. The method as set forth in claim 21, and further comprising the additional step of:
   moving said blade member from said extended position to said retracted position; and
   withdrawing said probe from said blood vessel.

23. A valvulectome adapted for use in excising a venous valve, comprising:
   an elongated probe having one end adapted to be inserted generally longitudinally into a vein, having another end adapted to remain outside said vein, and having an outer surface extending between said ends;
   recess means forming a recess extending into said probe from said outer surface adjacent said one end;
   a blade member movably mounted on said probe, said blade member having a cutting edge;
   actuating means mounted on said probe and selectively operable to cause said blade member to move relative to said probe between an outwardly-extended position in which said cutting edge is arranged outwardly beyond said outer surface, and an inwardly-retracted position in which said cutting edge is arranged within said recess; and
   a velocity sensor mounted on said probe for measuring the velocity of blood in said vein at the position of said sensor;
   whereby, when said blade member is in such retracted position, said cutting edge thereof will not extend outwardly beyond said outer surface, such that said probe may be moved longitudinally relative to said vein without causing undue damage to the endothelial tissue of said vein.

24. A valvulectome as set forth in claim 23 wherein said velocity sensor includes an indicator arranged outside said vein, and wherein said sensor and said indicator are connected by at least one electrical conductor.

25. A valvulectome as set forth in claim 23 wherein said velocity sensor is a piezoelectric element.

* * * * *